(12) United States Patent
Mashin-Chi et al.

(10) Patent No.: US 10,568,778 B2
(45) Date of Patent: Feb. 25, 2020

(54) SYSTEM AND METHOD FOR DETERMINING A PRE-EXISTING CHARACTERISTIC AND PRE-EXISTING STATE OF AN ARTICLE

(71) Applicant: Fred Bergman Healthcare Pty Ltd., North Sydney (AU)

(72) Inventors: Hadi Mashin-Chi, North Bondi (AU); Peter Hubertus Aigner, Killara (AU); Peter Curran, Oatley (AU); Mehdi Azimi, Lindfield (AU); Mohammed Asef Ali, Wentworthville (AU)

(73) Assignee: Fred Bergman Healthcare Pty Ltd., North Sydney (AU)

(*) Notice: Subject to any disclaimer, the term of this patent is extended or adjusted under 35 U.S.C. 154(b) by 1142 days.

(21) Appl. No.: 14/737,861

(22) Filed: Jun. 12, 2015

(65) Prior Publication Data
US 2016/0361209 A1 Dec. 15, 2016

(51) Int. Cl.
*A61F 13/42* (2006.01)

(52) U.S. Cl.
CPC ........ *A61F 13/42* (2013.01); *A61F 2013/424* (2013.01)

(58) Field of Classification Search
CPC ............................ A61F 13/42; A61F 2013/424
See application file for complete search history.

(56) References Cited

U.S. PATENT DOCUMENTS

| 2005/0033250 A1* | 2/2005 | Collette | A61F 13/42 604/361 |
| 2005/0156744 A1* | 7/2005 | Pires | A61F 13/42 340/573.5 |

(Continued)

*Primary Examiner* — Alexander Satanovsky
(74) *Attorney, Agent, or Firm* — Mauriel Kapouytian Woods LLP; Serge Krimnus

(57) ABSTRACT

The present invention relates to systems, methods and devices for determining one or more pre-existing characteristics, pre-existing states or both of a combination absorbent article and electrical circuit after connecting an electronic device to the combination absorbent article and electrical circuit. The method and system is particularly, although not exclusively, suitable for determining pre-existing characteristics such as absorbent article size, type, capacity and a pre-existing state such as whether or not the electrical circuit of the combination absorbent article and electrical circuit has been previously connected to the electronic device or another like electronic device. These pre-existing characteristics, pre-existing states or both are derived from measured electrical variables of the electrical circuit which may include one or more components, such as a resistor or a capacitor or a variable such as charge on a capacitor after the connection of an electronic device, which may include a transmitter or a transceiver. The method includes: measuring an electrical variable after connection of an electronic device to the combination article and electrical circuit to generate data indicative of the electrical variable at sequential time values; and processing the data with a processor including applying an If-Then rule based function comprising two or more conditions to determine a pre-existing characteristic, a pre-existing state or both of the combination absorbent article and electrical circuit.

19 Claims, 7 Drawing Sheets

(56) References Cited

U.S. PATENT DOCUMENTS

| | | | | |
|---|---|---|---|---|
| 2007/0049881 A1* | 3/2007 | Ales, III | ................ | A61F 13/42 604/361 |
| 2010/0085155 A1* | 4/2010 | Boss | ..................... | H04Q 9/00 340/10.1 |
| 2014/0350503 A1* | 11/2014 | Bosaeus | ................ | A61F 13/42 604/361 |

* cited by examiner

SYSTEM AND METHOD FOR DETERMINING A PRE-EXISTING CHARACTERISTIC AND PRE-EXISTING STATE OF AN ARTICLE

TECHNICAL FIELD

The present invention relates to systems, methods and devices for determining one or more pre-existing characteristics, pre-existing states or both of a combination absorbent article and electrical circuit after connecting an electronic device to the combination absorbent article and electrical circuit. The method and system is particularly, although not exclusively, suitable for determining pre-existing characteristics such as absorbent article size, type, capacity and a pre-existing state such as whether or not the electrical circuit of the combination absorbent article and electrical circuit has been previously connected to the electronic device or another like electronic device. These pre-existing characteristics, pre-existing states or both are derived from measured electrical variables of the electrical circuit which may include one or more components, such as a resistor or a capacitor or a variable such as charge on a capacitor after the connection of an electronic device, which may include a transmitter or a transceiver.

BACKGROUND OF INVENTION

Incontinence is a condition characterised by the uncontrolled release of bodily discharges from the bladder and/or the bowel. Urinary incontinence refers to loss of bladder control resulting in involuntary or uncontrolled urination. Urinary incontinence is a condition that is particularly prevalent among infants as well as in the elderly and infirm and, at least in relation to adult sufferers, is more prevalent among women.

Incontinence sufferers in care institutions such as hospitals, nursing homes, aged care facilities and geriatric institutions are cared for by the provision of absorbent articles such as pads, diapers, and the like. Carers in care institutions must periodically and manually check absorbent articles worn by subjects to determine whether an incontinence event has occurred, the extent to which the absorbent article has been filled and whether changing of the article is required.

Incontinence in infants in child-care facilities is also managed by the provision of diapers. Absorbent articles for absorbing liquids can also be used for other purposes including but not limited to menstrual pads and wound care articles. In these examples, periodic and manual checking of absorbent articles is required where the articles are diapers worn by infants in child-care facilities, or where the articles are menstrual pads or wound care articles worn by subjects in a care facility such as a hospital.

Incontinence indicators and detection systems including sensors in absorbent articles exist. Such systems can include sensors that are adapted for electrical connection to an electronic device which sends a signal to a processing device when an incontinence event is occurring or has occurred in the absorbent article. The signal processing device is configured to receive signals from one or more of such electronic devices and to process the signals to determine characteristics of incontinence events which are occurring or have occurred. Such systems may be adapted to alert a carer to the occurrence of an incontinence event so that the carer may check the article and, if necessary, change the article. Upon changing an absorbent article the sensor device in the new article is connected to the electronic device so that monitoring may continue with respect to the new absorbent article.

Existing incontinence monitoring systems are deficient in that after connection of the new absorbent article and sensor device they merely monitor incontinence activity. These systems are incapable of determining anything about the absorbent article and sensor device being connected to the electronic device such as whether the absorbent article and sensors have previously been used, the size or capacity of the absorbent article and sensor device, the type of absorbent article and sensor device, and other relevant information about the absorbent article and sensor device being connected to the electronic device. Similar limitations apply to monitoring systems in respect of other absorbent articles such as diapers, menstrual pads and wound care articles.

The present invention aims to improve upon systems and methods for monitoring combination absorbent article and sensor devices.

The above discussion of background art is included to explain the context of the present invention. It is not to be taken as an admission that any of the documents or other material referred to was published, known or part of the common general knowledge in the patent area at the priority date of any one of the claims of this specification.

SUMMARY OF INVENTION

In one aspect, the present invention provides a method for determining a pre-existing characteristic, a pre-existing state or both of a combination absorbent article and electrical circuit after connection of an electronic device to the combination absorbent article and electrical circuit. The method includes: measuring an electrical variable after connection of an electronic device to the combination article and electrical circuit to generate data indicative of the electrical variable at sequential time values; and processing the data with a processor including applying an If-Then rule based function comprising two or more conditions to determine a pre-existing characteristic, a pre-existing state or both of the combination absorbent article and electrical circuit.

Embodiments of the method are adapted to ascertain unknown a pre-existing characteristics, pre-existing states or both of a combination absorbent article and electrical circuit from electrical characteristics of the electrical circuit in the article. In some embodiments, the method is adapted to ascertain unknown characteristics of a combination absorbent incontinence article and electronic component, which may include a sensor array, from electrical characteristics of one or more electrical components in the electrical circuit and/or the sensor array thereof. The method and system is particularly, although not exclusively, suitable for determining a pre-existing characteristic such as absorbent article and/or sensor size, capacity, type or a pre-existing state such as whether or not the electrical circuit of the combination absorbent article and electrical circuit has been previously connected to the electronic device or another like electronic device from variables measured after connection of an electronic device to the combination article and electrical circuit. The electrical variable can include any one or more of capacitance of a capacitor and resistance of a resistor in the electrical circuit, voltage, current and charge stored on a capacitor.

In embodiments, the conditions include thresholds. Preferably, the thresholds are fixed or adaptive.

In embodiments, the step of processing the data includes applying a curve fitting function to the data generate extracts and the If-Then rule based function includes comparing the extracts to the two or more thresholds. Preferably, the extracts include parameters of a curve of best fit.

In embodiments, the If-Then rule based function includes comparing the data to the one or more thresholds. Preferably, each of the thresholds determines one or more state transitions in a state machine.

In embodiments, time intervals between consecutive time values are fixed or adaptive.

Preferably, the time intervals between consecutive time values are shorter during an early phase after connection of the electronic device to the combination article and electrical circuit than during a later phase.

In embodiments, the pre-existing characteristic or pre-existing state or both includes any one or more of: whether or not the electrical circuit of the combination absorbent article and electrical circuit has been previously connected to the electronic device or another like electronic device; size of the absorbent article and the electrical circuit or size of the electrical circuit; capacity of the absorbent article and the electrical circuit; and type of the absorbent article and the electrical circuit or type of the electrical circuit.

Preferably, the type of the absorbent article and the electrical circuit or the type of the electrical circuit includes any one or more of absorbent article construction information and absorbent article and/or electrical circuit manufacturer information.

Embodiments of the If-Then rule based function comprise two or more conditions, preferably in the form of thresholds, to determine the pre-existing characteristic, the pre-existing state or both of the combination absorbent article and electrical circuit.

In an embodiment of the If-Then rule based function, if the data is below one of the thresholds after connection of the electronic device to the combination article and electrical circuit and if the data subsequently exhibits an increasing trend that is greater and/or less than another one or more thresholds then the If-Then rule based function determines that the electrical circuit of the combination absorbent article and electrical circuit has not been previously connected to the electronic device.

In an embodiment of the If-Then rule based function, if the data is above one of the thresholds after connection of the electronic device to the combination article and electrical circuit and if the data subsequently exhibits an increasing trend that is greater and/or less than another one or more thresholds then the If-Then rule based function determines that the electrical circuit of the combination absorbent article and electrical circuit has been previously connected to the electronic device.

In an embodiment of the If-Then rule based function, if the data is between two thresholds after connection of the electronic device to the combination article and electrical circuit then the If-Then rule based function determines the size or capacity of the absorbent article and the electrical circuit or size of the electrical circuit.

The method can further include transmitting the determined pre-existing characteristic or the pre-existing state or both of combination article and electrical circuit, or information indicative thereof, to an electronic device for presentation to a user.

In embodiments, the method further includes utilising the determined pre-existing characteristic or the pre-existing state or both of the combination article and electrical circuit in a method and or system for determining any one or more of: the occurrence of wetness events in the absorbent article; wetness event volume for a wetness event occurring in the absorbent article; and that a combination absorbent article and electrical circuit being worn by a subject requires changing.

The method can further include wherein processing the data includes generating a plurality of pre-existing states at respective times and determining the pre-existing state includes selecting a subset from the plurality of pre-existing states. The aforementioned embodiment is adapted to filter out one or more of a plurality of pre-existing states that may be generated by the step of processing the data to thereby determine, more accurately, the actual pre-existing state of the combination absorbent article and electrical circuit, such as whether or not the electrical circuit of the combination absorbent article and electrical circuit has been previously connected to the electronic device or another like electronic device.

In another aspect, the present invention provides a system for determining pre-existing characteristic or the pre-existing state or both of a combination absorbent article and electrical circuit after connection of an electronic device to the combination absorbent article and electrical circuit, the system including: a combination absorbent article and electrical circuit; an electronic device connectable to the combination absorbent article and electrical circuit for measuring an electrical variable after connection of the electronic device to the combination article and electronic component to generate data points indicative of the electrical variable at sequential time values, and wherein the data points are processed by the application of an If-Then rule based function comprising two or more conditions to determine pre-existing information about the combination article and electrical circuit.

The system can include a processor for utilising the pre-existing characteristic or the pre-existing state or both of the combination article and electrical circuit for determining any one or more of: the occurrence of wetness events in the absorbent article; wetness event volume for a wetness event occurring in the absorbent article; and that a combination absorbent article and electrical circuit being worn by a subject requires changing.

In embodiments, the system includes a display for displaying the pre-existing characteristic or the pre-existing state or both of the combination article and electrical circuit for presentation to a user.

The system can also include a mobile electronic device including a display for receiving and displaying the pre-existing characteristic or the pre-existing state or both of the combination article and electrical circuit for presentation to a user.

The If-Then rule based function can include a rule which compares the data or the extracts to any one or more of a threshold, maxima and/or minima, values, transitional conditions or percentages for determining the pre-existing characteristic, state or both of the combination absorbent article and electrical circuit. In embodiments, the thresholds, maxima and/or minima, values, transitional conditions and percentages are predetermined or are fixed or are adaptive meaning they can be determined in a training process or determined and/or refined and/or improved in an optimization process. With the thresholds, maxima and/or minima, values, transitional conditions or percentages, which have been determined by a training process using training data obtained from absorbent article and electrical circuit combinations having known pre-existing characteristics or states, the method is capable during what could be described as an assessment phase of determining unknown pre-existing characteristics or pre-existing states or both of a combination absorbent article and electronic component, such as an absorbent article and sensor device combination including a wetness sensor array. The If-Then rules based function can include conducting a plurality of comparisons of one or more of the data or the extracts with any one of more of the thresholds, maxima and/or minima, transitional conditions or percentages and depending on the combination of outcomes of the plurality of comparisons determining the pre-existing characteristic, state or both of the combination absorbent article and electrical circuit. The If-Then rules based function can include conducting a plurality of comparisons of one or more of the data or the extracts to a plurality of thresholds, wherein if a first data point or extract is less than or greater than a first threshold and a second data point or extract is less than or greater than another threshold and so on then one or more pre-existing characteristics, states or both of the combination absorbent article and electrical circuit can be determined.

Preferably, the If-Then rule based model comprises a rule which compares the data or the extracts to any one or more thresholds to determine if the measured electrical variable is indicative of consecutive disconnections between the electronic device and the combination article and electrical circuit (e.g. such as might arise from an incomplete or unstable electrical connection between electrical contacts) followed by data or an extract below a threshold or indicative of a measured variable below a threshold with successive increasing data or extracts indicative of an increasing measured variable to determine that the combination article and electrical circuit has not been previously connected to the electronic device or another like electronic device. The If-Then rule based model can comprise a rule which compares the data or the extracts to one or more thresholds to determine if the measured electrical variable is indicative of consecutive disconnections between the electronic device and the combination absorbent article and electrical circuit followed by data or an extract above a threshold or that is indicative of a measured variable above a threshold and with successive increasing data or extracts indicative of an increasing measured variable to determine that the combination article and electrical circuit has been previously connected to the electronic device.

In some embodiments, the electrical variable is processed to generate the data and the function is applied to the data to generate the extracts. Preferably, the data includes a plurality of data points each including a time value and/or a sequence identification value and a magnitude value indicative of the measured electrical variable at each time interval.

The data preferably include magnitude values indicative of the signal received at each time interval. The data, and/or the magnitude values thereof, are preferably normalised.

The extracts are useful in determining a "signature" of the measured electrical variable and, therefore, of the pre-existing characteristic or pre-existing state of the electrical circuit.

Preferably, the pre-existing characteristic or pre-existing state of the combination absorbent article and electrical circuit includes a pre-existing characteristic or pre-existing state discernible from one or more electrical variables. Accordingly, the electrical variables of the combination absorbent article and electrical circuit may correlate by design or otherwise with pre-existing characteristics or states such as combination absorbent article and electrical circuit size, type, capacity and usage status (i.e. whether the combination absorbent article and electrical circuit has previously been connected to the electronic device), the manufacturer of the combination absorbent article and electrical circuit and various other properties that may be of interest.

Embodiments of the invention allow for automatic detection of the abovementioned pre-existing characteristics or status. Automatic detection of such pre-existing characteristics or status is advantageous as it can be utilised in a wetness event occurrence or wetness event volume estimation method and/or system adapted to detect wetness events and estimate wetness event volume for wetness events occurring in the absorbent article from a wetness event related electrical variable (e.g. sensor signals from wetness sensors) or data indicative of the wetness event related electrical variable used in the event detection or volume estimation method or system. Automatic detection of such pre-existing characteristics or status is advantageous in improving the efficiency and accuracy in the wetness event detection volume estimation methods and systems and other methods and systems that indicate time to change the absorbent article and electrical device combination and the like.

In embodiments, the method and the system includes transmitting the pre-existing characteristic or the pre-existing status of the absorbent article and electrical circuit combination, or information indicative thereof, to a mobile electronic device and displaying the pre-existing characteristic or the pre-existing state or both on a visual display component of the mobile electronic device. In embodiments in which the combination article and electrical circuit includes an absorbent article and sensor array and the mobile electronic device is a mobile device carried by a carer in a care facility the method and system allows for the carer to be provided with information about pre-existing characteristics or a pre-existing state or both of the absorbent article and sensor device combination, such as absorbent article size, type, capacity and whether the absorbent article and sensor array has been used previously or has previously been connected to the portable electronic device, the manufacturer of the article and various other pre-existing characteristics that may be of interest. Such information may be used to alert a carer to a mistake having been made such as having reconnected a previously used absorbent article and sensor array to the portable electronic device.

Preferably, the electronic device is a portable/wearable device adapted to, at least in part, measure the electrical variable after connection with the electrical circuit.

Preferably, the electronic device is a portable/wearable device including a transmitter for transmitting a signal or information indicative of the electrical variable to the processor.

Preferably, the system includes a transmitter for transmitting to a mobile electronic device the pre-existing characteristic or the pre-existing state or both, or information indicative thereof, of the combination article and electrical circuit for display by the mobile electronic device on a visual display.

In another aspect, the present invention provides an incontinence monitoring system for determining a pre-existing characteristic or pre-existing state or both of a combination absorbent article and electrical circuit after connection of an electronic device to the combination absorbent article and electrical circuit, the system including: a combination absorbent article and electrical circuit including a sensor for detecting an incontinence event in the absorbent article; an electronic device connectable to the combination absorbent article and electrical circuit for measuring an electrical variable after connection of the electronic device to the combination article and electronic component to generate data points indicative of the electrical variable at sequential time values; wherein the data points are processed by the application of an If-Then rule based function comprising two or more conditions to determine the pre-existing characteristic or the pre-existing state or both of the combination article and electrical circuit.

In some embodiments, the generation of data points indicative of the electrical variable at sequential time values and/or processing is carried out in part or in full by a processor contained in the portable electronic device.

In some embodiments, the generation of data points indicative of the electrical variable at sequential time values and/or processing is carried out in part or in full by a processor contained in a server.

In some embodiments, a transmitter, incorporated in the portable electronic device or coupled to the server, transmits to a mobile electronic device information indicative of the pre-existing characteristic or status or both of the combination absorbent article and electrical circuit for display by the mobile electronic device.

BRIEF DESCRIPTION OF DRAWINGS

The invention will now be described in more detail with reference to the accompanying Figures which are illustrative of embodiments and examples thereof. It is to be understood that the particulars of the Figures are not to be construed as limiting to the generality of the invention described above.

DETAILED DESCRIPTION

Figure 1:
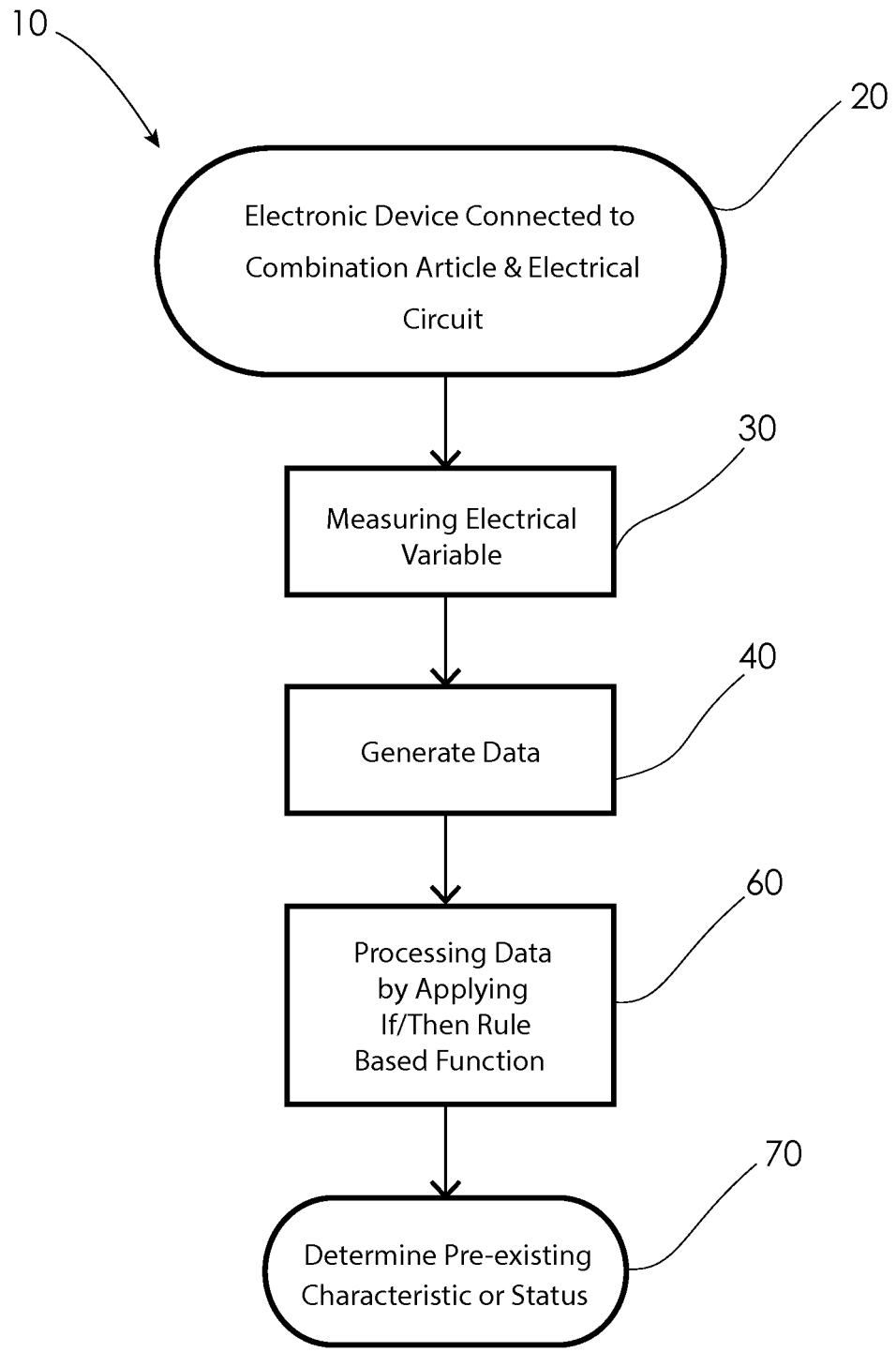
FIG. 1 illustrates a method in accordance with an embodiment of the invention, wherein the method is for determining a pre-existing characteristic, a pre-existing state or both of a combination absorbent article and electrical circuit such as a wetness sensor, after the connection of an electronic device thereto.

Referring to FIG. 1, an embodiment of the invention is illustrated in the form of a method 10 for determining a pre-existing characteristic of a combination absorbent article and electrical circuit after the connection of an electronic device to the combination absorbent article and electrical circuit at 20. In embodiments of the invention disclosed herein, the combination absorbent article and electrical circuit includes an absorbent article and a wetness sensor, which may include a sensor array and other electronic components. In embodiments of the invention disclosed herein, the electronic device may be a portable and/or wearable device, which may include a transceiver, a transmitter or a receiver that is connected to the article. In other embodiments, the electronic device may not be portable but rather may be an installed system including a gate that communicates wirelessly with the combination absorbent article and electrical circuit such as with radio communication signals or other wireless communication means.

As further illustrated in FIG. 1, the embodiment of the method 10 includes measuring an electrical variable after connection of the electronic device to the combination absorbent article and electrical circuit at 30. The data is generated at 40 from the measured electrical variable or information indicative of the measured electrical variable. The data may be generated by a processor on the portable electronic device or via a remote processor. The data is processed by applying an If-Then rule based function at 60 to determine the pre-existing characteristic, the pre-existing state or both of the combination absorbent article and electrical circuit at 70.

Figure 2:
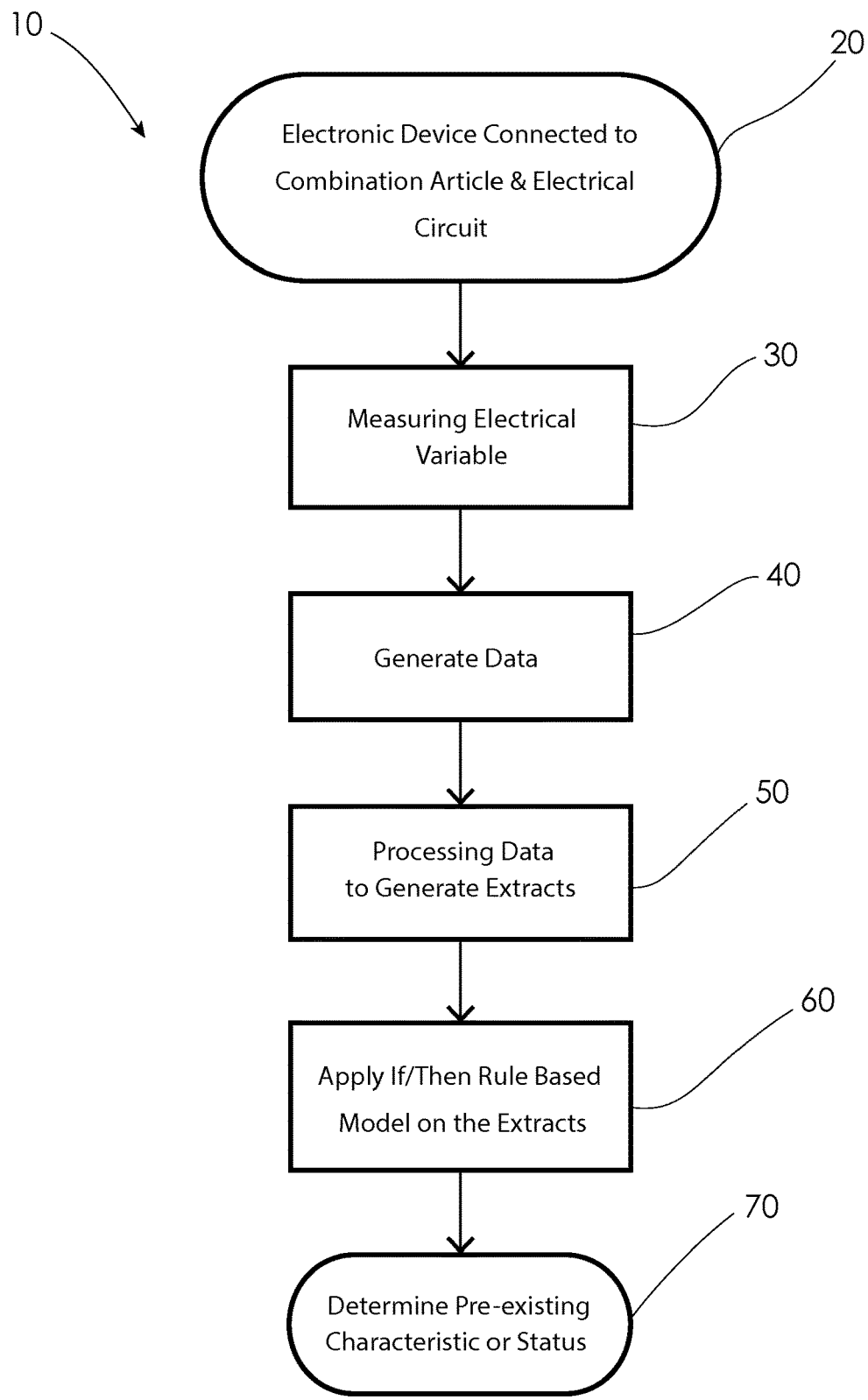
FIG. 2 illustrates a method in accordance with another embodiment of the invention, wherein the method is for determining a pre-existing characteristic, a pre-existing state or both of a combination absorbent article and electrical circuit such as a wetness sensor, after the connection of an electronic device thereto.

In FIG. 2 illustrates an embodiment of the method involving the application of a curve fitting function to the data generated from the measured variable. The embodiment of the method 10 of FIG. 2 includes determining a pre-existing characteristic, a pre-existing state or both of a combination absorbent article and electrical circuit after connection of an electronic device to the combination article and electrical circuit at 20. The electronic device measures an electrical variable after connection of the electronic device to the combination absorbent article and electrical circuit at 30. The electronic device may include a processor adapted to carry out part or all of the processing functions illustrated in FIG. 2. Accordingly, in the embodiment of FIG. 2, the measured electrical variable or information indicative of the electrical variable is used to generate data indicative of the electrical variable at 40. The data is then processed, such as by the application of a curve fitting function, at 50 to generate extracts which are variables of the curve fitting function. An If-Then rule based model is applied to the extracts at 60 to determine the pre-existing characteristic, the pre-existing state or both of the combination absorbent article and electrical circuit at 70.

In the embodiment of FIG. 1, the data processed by the application of the If-Then rule based function can be the raw, unprocessed measured variable or extracts derived from the data through the application of the curve fitting function. However, in FIG. 2, the extracts derived from the data through the application of the curve fitting function are processed by the application of the If-Then rule based function. The data may include the magnitude of variable, such as voltage, current and/or any other electrical variable such as capacitance, resistance, or charge on a capacitor at consecutive time values. Each data point includes a time value and/or sequence identification value and a magnitude value indicative of the magnitude of the variable. The time or sequence identification value may include an integer or sequence number or time stamp or the like. The magnitude value may include an integer representative of voltage, current, resistance, capacitance, and/or charge on a capacitor. The magnitude values may be normalised by being adjusted according to a notionally common scale. The time values and/or the intervals between time values may be fixed or adaptive and may initially be determined in a training process.

In embodiments in which the combination absorbent article and electrical circuit includes a sensor device in an absorbent article, the pre-existing characteristic, the pre-existing state or both includes any one or more of: connection state, which refers to whether or not the combination absorbent article and electrical circuit has been previously used or previously connected to the electronic device; absorbent article and electrical circuit size; absorbent article capacity; and absorbent article and electrical circuit type/construction and manufacturer information.

Figure 3:
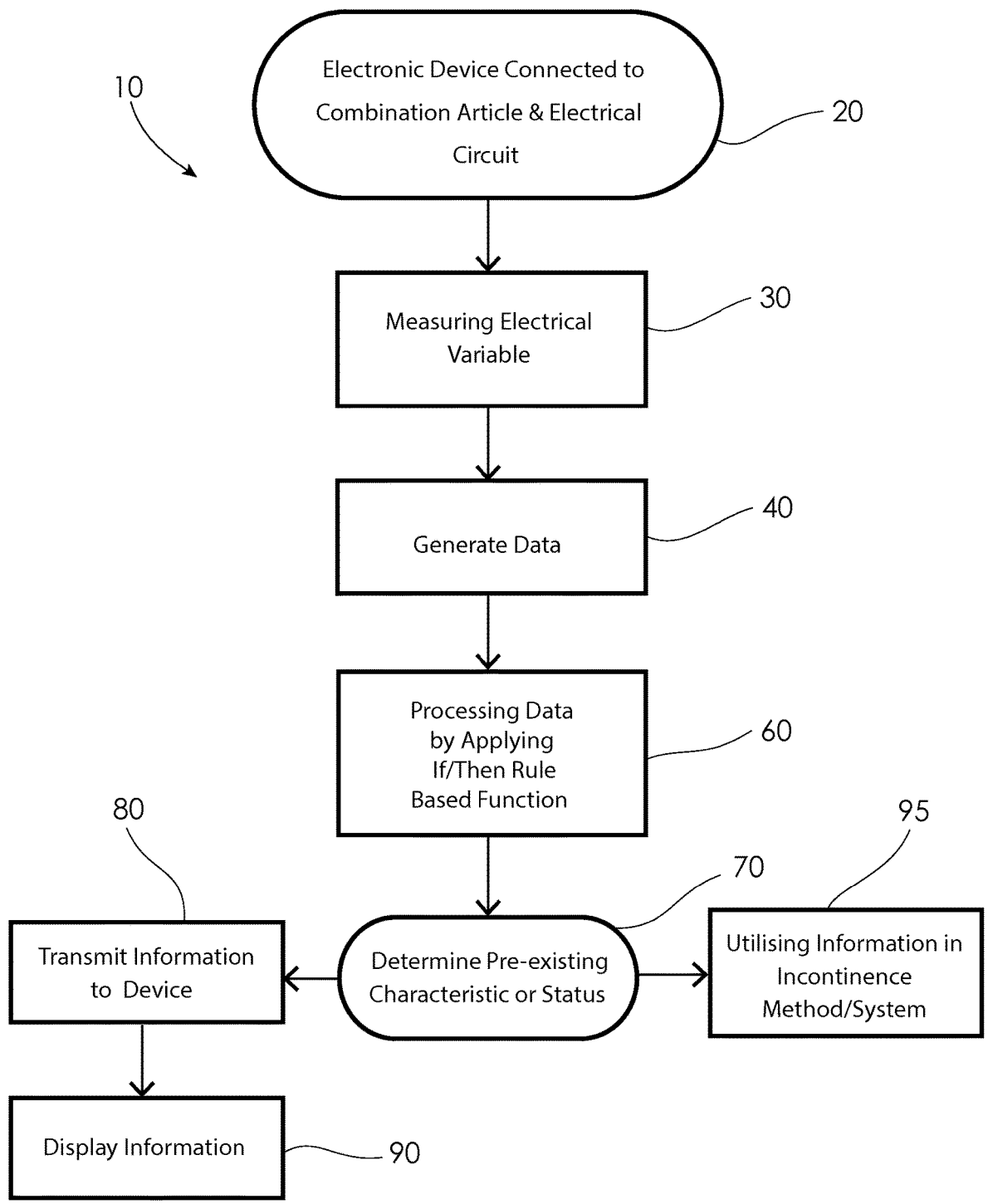
FIG. 3 illustrates embodiments of the method of FIGS. 1 and 2 in which the method is for determining a pre-characteristic of a combination absorbent article and electrical circuit after the connection of an electronic device thereto.

Referring to FIG. 3, which illustrates further embodiments of the method, which includes the steps of the embodiments of FIGS. 1 and 2 and further including the steps of transmitting information indicative of the determined pre-existing characteristic of the absorbent article and sensor device combination to an electronic device such as a mobile electronic device at 80 and displaying the information on a visual display device component of the electronic device at 90. In embodiments in which the combination article and electrical circuit includes an absorbent article and sensor device and the mobile electronic device is a mobile device carried by a carer in a care facility the method allows for the carer to be provided with information about pre-existing characteristics, pre-existing state or both of the absorbent article and sensor device combination, such as article size, article type, article usage state (i.e. whether the article has been used previously or has previously been connected to the electronic device), article capacity, the manufacturer of the article and various other properties of the article that may be of interest. Such information may be indicative of the carer making a mistake such as having reconnected a previously used absorbent article and sensor device to the electronic device.

Referring to FIG. 3, which illustrates an embodiment including the step of utilising the determined pre-existing information about the combination article and electrical circuit in an incontinence detection method and or system at 95. The incontinence detection method and or system can be for determining any one or more of: the occurrence of wetness events in the absorbent article; wetness event volume for a wetness event occurring in the absorbent article; and that a combination absorbent article and electrical circuit being worn by a subject requires changing. As mentioned above, the method is advantageous as it can enable improvements in efficiency and accuracy in the detection and determination of characteristics of wetness events detected by a sensor device in an absorbent article, such as occurrence of wetness events, wetness event volume, time to change the absorbent article and sensor combination and the like.

System

Figure 4:
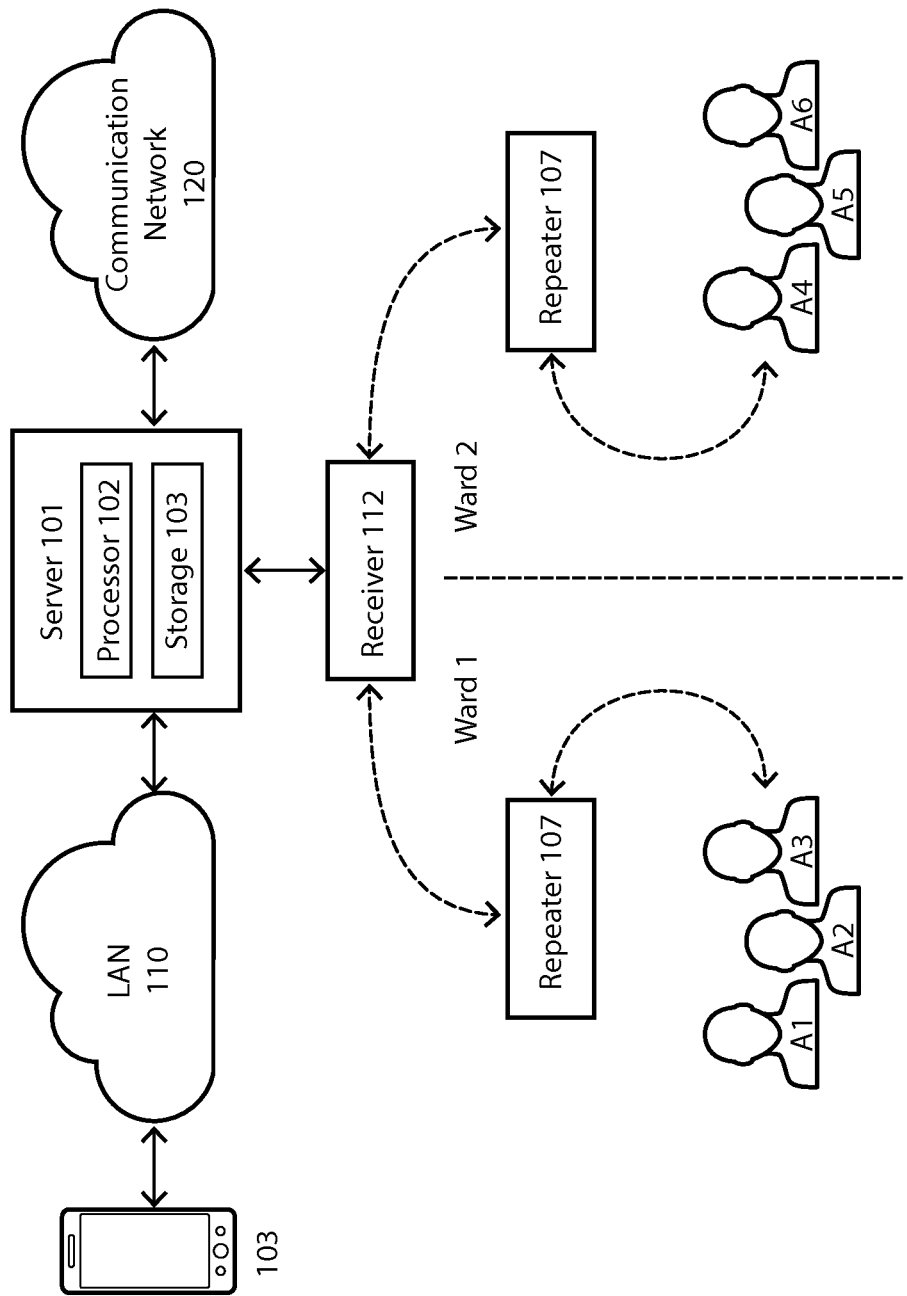
FIG. 4 illustrates a system for determining a pre-existing characteristic, a pre-existing state or both of a combination absorbent article and electrical circuit, comprising part of an incontinence monitoring system in accordance with an embodiment of the invention that is employed in a care facility such as an aged care facility, hospital, or a child-care facility.

FIG. 4 illustrates an incontinence monitoring system 100 in accordance with an embodiment of the invention that is employed in a care facility such as an aged care facility, hospital, child-care, or other care facility. The system 100 is particularly adapted for monitoring incontinence in a number of subjects 104. The system 100 includes a server 101 including a processor 102 and a storage medium 103. The system 100 includes a receiver 112 that is adapted to receive signals from portable electronic devices A1-A6 associated with each of the subjects 104 being monitored by the system 100. The signals from the portable electronic devices A1-A6 may be transmitted to a repeater 107 located in a ward containing the subjects 104 which may then re-transmit the signals to the receiver 112. The server 101 may be co-located with the receiver 112 in the facility or may be located remotely and connected to the receiver 112 via a network.

Figure 5:
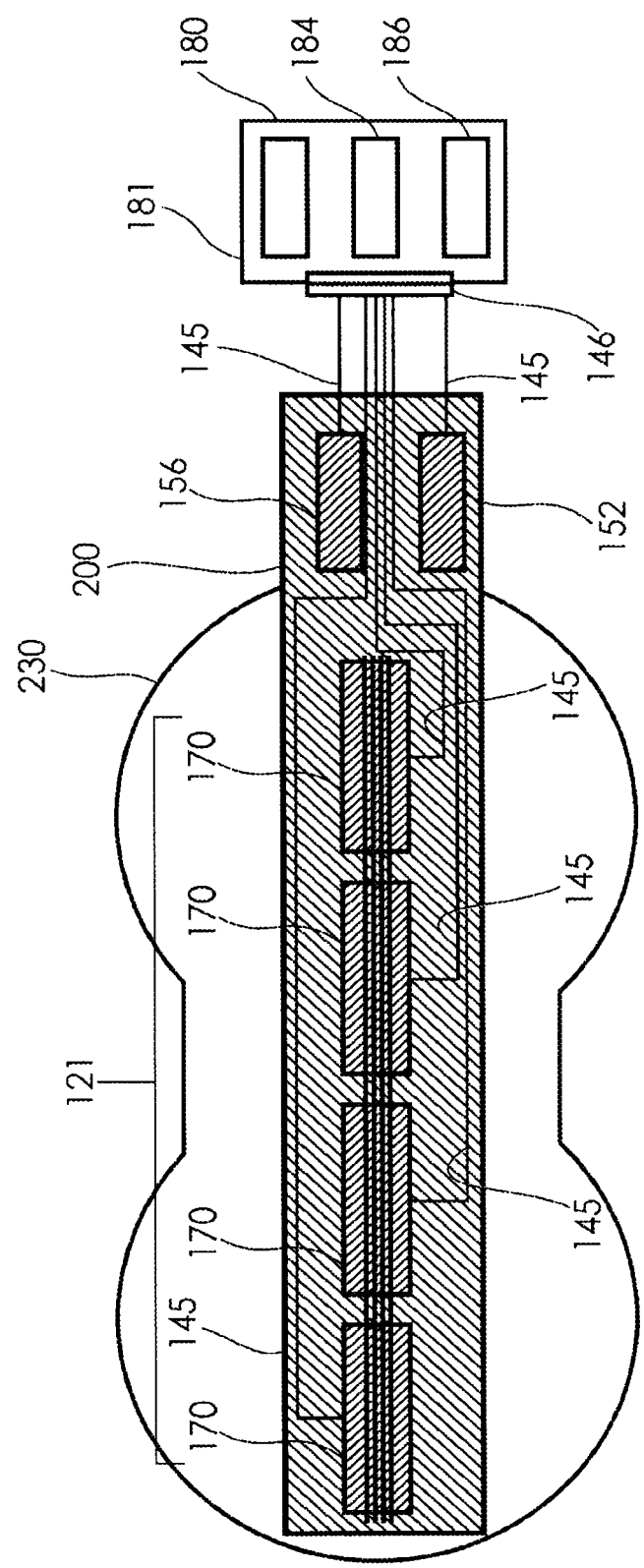
FIG. 5 illustrates an embodiment of a combination absorbent article and electrical circuit and a wetness sensor and a electronic device connected thereto.

An exemplary form of each one of the portable electronic devices A1-A6 associated with each of the subjects 104 of FIG. 4 is illustrated in FIG. 5. The exemplary electronic device 180 includes a receiver 181, a processor 184 and a transmitter 186. In another embodiment, the exemplary electronic device 180 includes a receiver 181 and a transmitter 186. Each electronic device 180 is adapted to transmit and receive signals, preferably wirelessly, to and from the repeater 107 or otherwise directly to and from the receiver 112 of the system 100 of FIG. 4.

Referring to FIG. 5, the electronic device 180 includes one or more electrical connectors 182 for physical connection with electrical connectors 146 of an electrical circuit 200, such as an array of sensors 170, in or connected to an absorbent article 230. The electrical circuit 200 may include a sensor array 171 and electronic components attached to or in the absorbent article 230 during manufacture. The electrical circuit 200 may not include a sensor array and may, for example, simply include a resistor and/or capacitor. Upon connection between the connectors 182 of the electronic device 180 and the connectors 146 of the electrical circuit 200 the electronic device 180 is adapted to provide a signal source to the electrical circuit 200.

The electronic device 180 may be configured for wired (contact) connection or wireless (contactless) connection, such as by inductance or otherwise, with the electrical circuit 200. The composition of the electrical circuit 200 will be described in more detail below. However, it is to be appreciated that embodiments of the present invention are particularly, though not exclusively, directed towards determining characteristics of the combination absorbent article 230 and the electrical circuit 200, preferably including the sensor array 171, after connection with the electronic device 180.

The electrical circuit 200 may be attached to or be incorporated in the absorbent article 230 during manufacture or after manufacture. The electrical circuit 200, including the sensor array 171, typically detects wetness in the absorbent article 230 but may alternatively or additionally detect other parameters such as wetness, temperature, pH, presence of biological analytes or pathogens, pressure, or the like.

The server 101 is adapted to communicate via a local area network 110, such as a Wi-Fi network and/or via a mobile telecommunications network, with one or more mobile electronic devices 108 operated by a carer, such as a nurse or the like, within the care facility. The mobile electronic device 108 may be a dedicated mobile electronic device or may be a smart phone running an application configured for interoperability with the server 101 via the local area network 110, such as the Wi-Fi network, or via the mobile telecommunications network. The mobile electronic device 108 includes a display under the control of a processor and provides a visual representation of continence-related information obtained by monitoring wetness events occurring in the absorbent article 230 worn by a subject. A carer responsible for a subject being monitored uses the mobile electronic device 108 to receive alerts or to check the continence status of the subject by viewing the visual representation. The mobile electronic device 108 may also convey visual, audible or other haptic reminders to carers to check the continence state of a subject or to perform an absorbent article 230 change or assist the subject with a toileting event. The mobile electronic device 108 also includes an input component that enables the carer to operate the device 108 and, in certain circumstances, input data to the system 100 such as observations such as the absorbent article size, capacity, type, manufacturer as well as the sensor device type and also the weight of used absorbent articles 230 after changing. Such data input to the system 100 is used in some embodiments to provide training data during a training phase or for carrying out an optimization process. It is to be appreciated that such data may be input into the system 100 directly to the server 101 via an input device associated directly with the server. The mobile electronic device 108 may be customised for the system 100 or, otherwise, may be a smartphone device running one or more applications enabling it to be used with the system 100.

FIG. 5 illustrates an embodiment of an absorbent article 230 adapted to be worn by a subject suffering from incontinence. The absorbent article 230 includes the electrical circuit 200 therein. The electrical circuit 200 includes an array of the sensors 170, preferably conductivity sensors, electrically connected via conductors 145 to an electrical connector 146. Each of the conductivity sensors 170 in the sensor array 171 has a known resistance. The electrical circuit 200 may, in addition to or instead of the sensor array 171, include a capacity circuit 156 which may comprise one or more resistors of known resistance and/or capacitors of known capacitance electrically connected via conductors 145 to the electrical connector 146. The electrical circuit 200 may, in addition to or instead of the sensor array 171 and capacity circuit 156, include a usage circuit 152 which may comprise one or more resistors of known resistance and/or capacitors of known capacitance electrically connected via conductors 145 to the electrical connector 146. The known resistance and capacitance values of the conductivity sensors 170, resistors and capacitors in the electronic device is employed in the system 100 and the method 10 of the present invention to determine pre-existing characteristics, a pre-existing state or both of the combination electrical circuit 200 and the absorbent article 230. Such characteristics include but are not limited to any one or more of whether the combination absorbent article 230 and the electrical circuit 200 have previously been used or not, that is whether the electrical circuit 200 has previously been connected to the electronic device 180 (also referred to herein as "usage state"), the size of the absorbent article 230 and electronic device 200 (e.g., small, medium or large), the capacity of the absorbent article 230 (e.g., light, medium or heavy), the manufacturer of the absorbent article 230 and/or the electrical circuit 200.

After connection between the electrical connector 146 of the electrical circuit 200 and the electrical connector 182 of the electronic device 180, electronic components of the electronic device 180 are adapted to measure electrical variables of the electrical circuit 200. Such electrical variables include voltage, current, resistance, capacitance or charge on a capacitor and are at least in part dependent on one or more components of the electrical circuit 200 and/or the capacity circuit 156 and or due to any residual charge in a capacitor in the usage circuit 152 in the electrical circuit 200. In circumstances in which the electrical circuit 200 associated with a particular absorbent article 230 has previously been connected to the electronic device 180 (i.e. previously used), the usage circuit 152 may contain a residual charge, such as in a capacitor. As such, when the electrical circuit 200 is connected to the electronic device 180 a measure electrical variable is processed and converted into data that is transmitted to the repeater 107 or the receiver 112 component of the system 100. The data may be indicative of a voltage and/or current at times which may be fixed or adaptive. The magnitude value of the data (which relates to the magnitude of the measured electrical variable) may include an integer representative of charge and/or voltage and/or current. The magnitude values may be normalised by being adjusted according to a notionally common scale. The time values may be fixed, adaptive or may be initially determined in a training process.

For reasons that will become apparent below, the processor 102 applies a function to the data to generate extracts that are indicative of one or more characteristics of the signal received by the electronic device 180 and, hence, one or more pre-existing characteristics, the pre-existing state or both of the combination electrical circuit 200 and absorbent article 230. As will be discussed in more detail below, the function that is applied to the data may include a curve fitting or a state machine function. It is to be appreciated that other functions may be applied to the data. In other embodiments, the processor 102 may not apply a function to the data to generate extracts but rather the signal itself comprises extracts from which to determine one or more pre-existing characteristics, the pre-existing state of the electrical circuit 200 and/or the absorbent article 230.

Signal Processing

Figure 6:
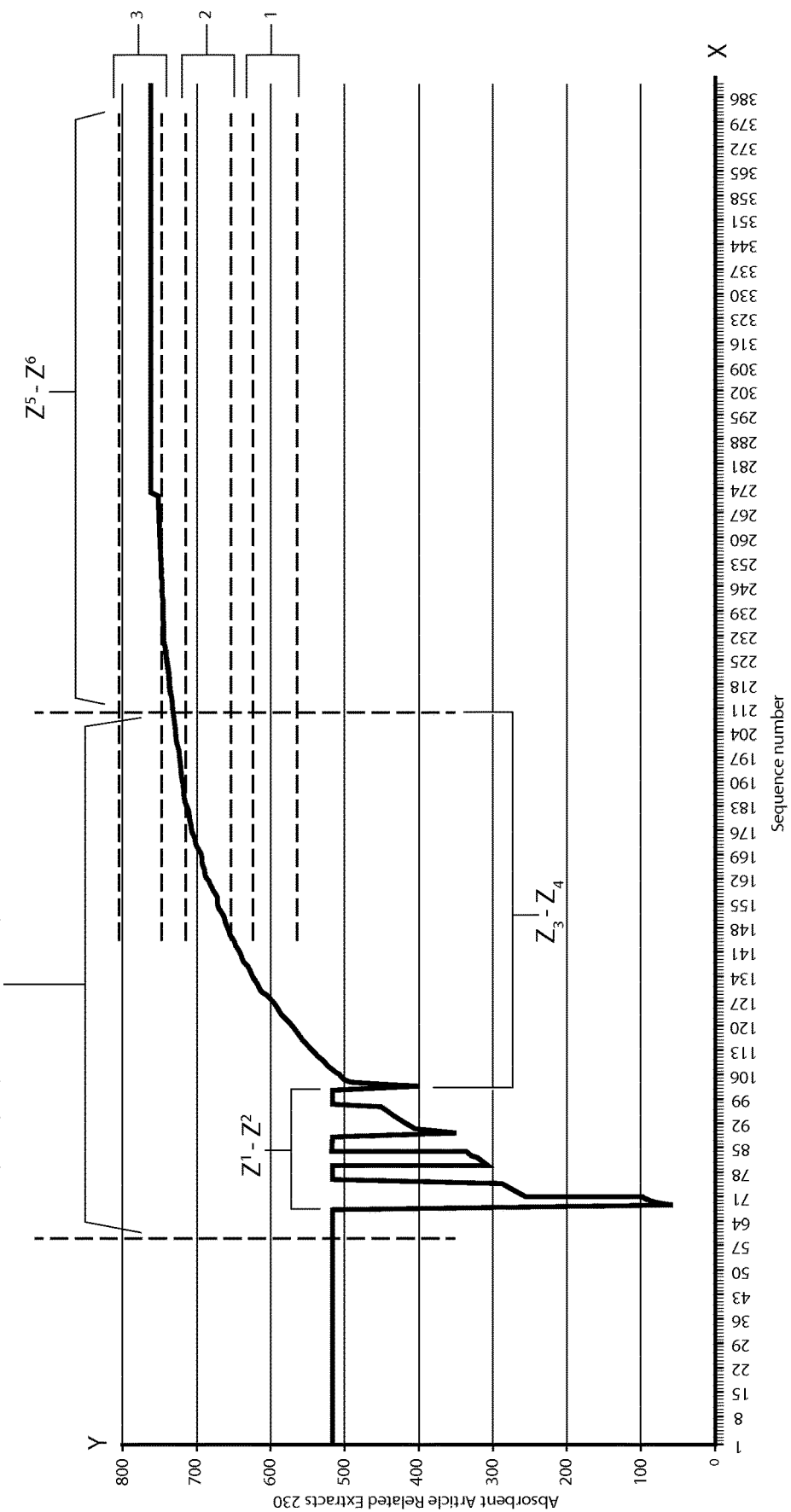
FIG. 6 illustrates an exemplary graph of data from an electrical variable measured after connection of a combination absorbent article and electrical circuit to an electronic device.

FIG. 6 illustrates an exemplary graph of data from a processed of an electrical variable measured after connection of the electronic device 180 to the electrical circuit 200. The data includes time stamped charge and/or voltage and/or current signal data which is received by the processor 102. The data is plotted with units of signal magnitude represented by the vertical axis and units of time or sequence identification represented by the horizontal axis.

It has been found that if the absorbent article 230 and electrical circuit 200 combination are previously unused (not previously connected) then the data at one or more of the first data points will, at least in most cases, indicate an initial magnitude below a threshold. Conversely, if the absorbent article 230 and electrical circuit 200 combination is previously used (previously connected) then the data at one or more of the first data points will, at least in most cases, indicate an initial magnitude above the threshold. Before, during or after such a data point there may be several data points indicating disconnections or no connection between the electronic device and the combination article and electronic component. Successive data points will indicate a rising trend until the magnitude reaches a steady state at which the magnitude of the data will indicate neither a rising nor a falling trend. After initial connection of the electronic device 180 and the electrical circuit 200 the signal received by the electronic device 180 may be unstable and may fluctuate as illustrated by the portion of data during phase $Z^1$ to $Z^2$ in FIG. 4. During this phase, the signal received by the electronic device 180 will include signals that are truly representative of the electrical behaviour of the electrical circuit 200 but will also include signals that are not truly representative of the electrical behaviour of the electrical circuit 200 or that are indicative of no connection at all between the electrical circuit 200 and the electronic device 180 (i.e. disconnections). Such a signal which may be considered an unstable or "bouncing" signal may be due to a loose connection.

As will become apparent, the data obtained during an initial period of time, such as 10, second, 20 seconds, 30 seconds, 40 second, or any increment thereof, after connection between the electrical circuit 200 and the electronic device 180 can provide an indication as to whether the electrical circuit 200 has previously been connected to the electronic device 180 (also referred to herein as "usage state"), the size of the absorbent article 230 (e.g., small, medium or large), the capacity of the absorbent article 230 (e.g., light, medium or heavy), the manufacturer of the absorbent article 230 and/or the electrical circuit 200 and other characteristics of interest. Automatic detection of the abovementioned information about the electrical circuit 200 and the absorbent article 230 is particularly advantageous in the system 100 as it can be automatic used in the incontinence monitoring system 100 in ways that improve incontinence monitoring outcomes. Automatic use of information such as pre-existing characteristics, pre-existing state or both is advantageous in improving efficiency and accuracy in the detection and determination of characteristics of wetness events detected by the electrical circuit 200 such as event volume and/or whether the article 230 requires changing.

The information indicative of the pre-existing characteristics, pre-existing state or both of the combination absorbent article and electrical circuit is utilised in a volume estimation method and/or system adapted to determine/estimate wetness event volume for a wetness event occurring in the absorbent article from a wetness event related electrical variable (e.g. sensor signals) or data indicative of the wetness event related electrical variable used in the volume estimation method or system. In addition, or alternatively, the information indicative of the pre-existing characteristic, the pre-existing state or both of the combination absorbent article and electrical circuit is utilised in a wetness event detection method and/or system adapted to determine/estimate the occurrence of wetness events in the absorbent article from a wetness event related electrical variable (e.g. sensor signals) or data indicative of the wetness event related electrical variable used in the wetness event detection method or system. In addition or alternatively, the information indicative of the pre-existing characteristics, the pre-existing state or both of the combination absorbent article and electrical circuit is utilised in a method or system for indicating that a combination absorbent article and electrical circuit being worn by a subject requires changing from a wetness event related electrical variable (e.g. sensor signals) or data indicative of the wetness event related electrical variable. The information indicative of the pre-existing characteristics, the pre-existing state or both of the combination absorbent article and electrical circuit usage state (e.g. previously used/connected or previously unused/not connected), and/or combination absorbent article and electrical circuit capacity (e.g. light, moderate, heavy) determines or selects one or more functions that, in the volume estimation method and/or system and/or wetness event detection method and/or system and/or method and/or system for indicating that a combination absorbent article and electrical circuit being worn by a subject requires changing, is applied to the wetness event related electrical variable (e.g. sensor signals) or the data indicative of the wetness event related electrical variable.

During an early phase after connection between the electrical circuit 200 and the electronic device 180, the electrical variable measurement frequency and associated data collection frequency may be higher than in later periods after the early phase. This is due to the fact that rate of change of the electrical variable measured by the electronic device 180 at the early phase after connection with the electrical circuit 200 will be higher than at later phases. Thus, to discern pre-existing characteristics, pre-existing state or both of the electrical circuit 200 from the rapidly changing signal received immediately after initial connection, such as "usage state", requires relatively frequent collection of data. In contrast, at later phases where pre-existing characteristics or pre-existing state of the electrical circuit 200 is discerned from a stable or steady signal, such as a size of the absorbent article 230 (e.g., small, medium or large), the capacity of the absorbent article 230 (e.g., light, medium or heavy), or the like, requires relatively less frequent collection of data. The point at which the frequency of data collection changes and the extent of any change of data collection frequency, in terms of intervals between data collection, is determined during a training process and may be optimized during an optimization process.

Referring to FIG. 6, it can be seen that a period of time after initial connection between the electrical circuit 200 and the electronic device 180, the electrical variable measured by the electronic device 180 tends to stabilise. The portion of data during phase $Z_3$ to $Z_4$ in FIG. 4 indicates a rising trend of a stable signal until a point in time after which the signal reaches equilibrium (i.e. neither rising nor falling). The portion of data during phase $Z^5$ to $Z^6$ indicates that a steady state has been reached at which the signal, and the data obtained therefrom, indicates neither a rising nor a falling trend. The magnitude or level of the electrical variable in the vertical axis during phase $Z^5$ to $Z^6$, which is the phase during which the magnitude stabilises, is indicative of one or more characteristics of the device 200 and/or the absorbent article 230.

Data Processing

In the embodiment illustrated in FIG. 6, the characteristic indicated by the magnitude of the electrical variable, in the vertical axis, at selected points in time and/or a rising or falling trend of the data during phase $Z^1$ to $Z^2$ can be indicative of one or more pre-existing characteristics or pre-existing status, such as whether the absorbent article 230 and or the electrical circuit 200 has previously been connected to the electronic device 180 and, therefore, whether the absorbent article 230 and or the electrical circuit 200 has previously been used. This pre-existing characteristics, pre-existing state or both of the absorbent article 230 and or the electrical circuit 200 can be referred to as "usage state". One or more other pre-existing characteristics, pre-existing state or both that may be indicated by the data during phase $Z^1$ to $Z^2$ may include the absorbent article size and/or absorbent article manufacturer information.

In the embodiment illustrated in FIG. 6, the pre-existing characteristics, pre-existing state or both indicated by the magnitude of the data, in the vertical axis, at selected points in time and/or a rising or falling trend of the data during phase $Z^5$ to $Z^6$ is substantially indicative of the capacity of the absorbent article 230, for example either light $X_1$, medium $X_2$ or heavy capacity $X_3$. The electrical response of componentry of the device 200 such as the number of sensors 170 in the array 171, the resistance of the sensors 170, the resistance of one or more resistors or the capacitance of one or more capacitors, or combinations thereof, in the absorbent article/pad capacity circuit 156 may correlate with the capacity of the absorbent article 230, namely either light, medium or heavy capacity. The electrical response of componentry of the device 200 such as the number of sensors 170 in the array 171, the resistance of the sensors 170, the resistance of one or more resistors or the capacitance of one or more capacitors, or combinations thereof, in the absorbent article/pad usage state circuit 152 may correlate with the usage state of the electrical circuit 200 and the absorbent article 230, namely either previously unused or previously used. The electrical response of componentry of the electrical circuit 200 such as the number of sensors 170 in the array 171, the resistance of the sensors 170, the resistance of one or more resistors or the capacitance of one or more capacitors, or combinations thereof, in the array of sensors 171, the article/pad capacity circuit 156 and/or the usage state circuit 152, may correlate with the size and/or manufacturer of the electrical circuit 200 and/or the absorbent article 230. Accordingly, one or more other characteristics that may be indicated by the data during phase $Z^5$ to $Z^6$ may include the absorbent article size and/or absorbent article manufacturer information.

Thus, the magnitude or level of the electrical variable in the vertical axis during phase $Z^1$ to $Z^2$, $Z_3$ to $Z_4$, and/or $Z^5$ to $Z^6$, may be indicative of any one or more of the above pre-existing characteristics, pre-existing state or both of the electrical circuit 200 and/or the absorbent article 230.

Curve Fitting

According to embodiments of the invention, after the electrical variable measured by the electronic device 180 after connection with the electrical circuit 200 is processed to generate data, a function is applied to the data to generate "extracts" indicative of one or more pre-existing characteristics, pre-existing state or both of the electrical circuit 200. Preferably, the function that is applied to the data may utilize a curve fitting procedure. The extracts can include parameters of a curve fitted to each set of data points derived from a single connection of the device 200 and/or absorbent article 230 with the electronic device 180. The curve-fitting approach can include a training phase that involves receiving a set of training data in relation to combinations of electronic components 200 and/or absorbent articles 230 with known characteristics such as "usage state", the size of the absorbent article 230 (e.g., small, medium or large), the capacity of the absorbent article 230 (e.g., light, medium or heavy, the manufacturer of the absorbent article 230 and/or the electrical circuit 200 and other characteristics.

The curve-fitting analysis may be performed for all the training data collectively or separately, for each of the sets of the previously unused and used electronic components 200 and/or absorbent articles 230. During the training process, curve-fitting is performed on the training data. Then, during an assessment phase, in order to detect previously unused and used electrical circuit 200 and/or absorbent article 230 combinations, parametric curve-fittings of the data obtained during the assessment phase using the same curve type derived during the training process, is performed to detect, for example, whether the devices 200 and/or absorbent articles 230 have previously been used or are previously unused.

The function may be determined by any suitable means and may be predetermined or derived during a training process. During a training process, a function is applied to training data obtained from electronic components 200 and/or absorbent articles 230 with known characteristics of interest. For example, a curve fitting function that is suitable for training data derived from signals generated after connection between an electronic device 180 and an electrical circuit 200 that produces data such as is illustrated in FIG. 6, is:

$$f(x) = a - b^{-\frac{cx-d}{g}}$$

The curve for each set of training data indicative of each connection between the electronic device 180 and the electrical circuit 200 can be represented by the coefficients which are a, b, c, d and g. These coefficients during the training process, known as the extracts, are indicative of the curve of best fit derived from the curve fitting function applied to the training data and, hence the characteristics of the article (i.e. the electrical circuit 200 and/or the absorbent article 230) of interest. In an embodiment one or more of these coefficients or extracts have one or more acceptable boundaries. The derived extracts and their acceptable boundaries are then used to generate an If-Then rule-based model.

In addition or in the alternative, a non-parametric curve fitting approach may be adopted to derive a function for a curve that fits the training data.

During an assessment phase, the same curve fitting function, which is applied during the training process, is applied to data obtained from electrical circuit 200 and absorbent article 230 combinations with unknown characteristics. The curve that is fitted to the data obtained during the assessment phase can be represented by its derived coefficients, referred to herein as "extracts", which are then to be evaluated with the If-Then rule-based model generated during the training process to identify the unknown pre-existing characteristics, pre-existing state or both of the electronic components 200 and/or absorbent articles 230 from data obtained from sensor signals received by the electronic device 180 from the electrical circuit 200 during the assessment phase. The acceptable boundaries can be set by trial-and-error or can be derived by measuring the variability or standard deviation of the averaged coefficients of all the models if data is used separately.

In an embodiment, the function and the extracts are derived and/or refined using an optimization procedure utilizing a set of training data obtained during a training process or using training data obtained during an assessment phase. Otherwise, the function and the extracts may be derived directly by knowing the electrical behaviour of the electrical circuit 200 as a function of the one or more characteristics of the electrical circuit 200 and/or the absorbent article 230.

In the following, curve-fitting and state machine functions are used to derive the pre-existing characteristics, pre-existing state or both of the electrical circuit 200 and associated absorbent article 230. Other methods such as independent component analysis (ICA), decision trees, neural networks, and the like may be applied in a similar manner. Then it is showed how both curve-fitting and the state machine examples may be converted into an If-Then rule-based.

If-Then Rule Based Model

In accordance with embodiments of the invention, during an assessment process, the extracts are derived either directly from the signals or by a curve fitting approach, and an If-Then rule-based model is applied to the extracts. In another embodiment, a state machine approach or the like may be employed and the extracts converted to an If-Then rule-based model. In relation to the curve fitting function example, the If-Then rule based model is applied to the extracts a, b, c, d and g, which are obtained by the parametric curve fitting, for each set of data indicative of each connection between the electronic device 180 and the electrical circuit 200 and its associated absorbent article 230. It is to be appreciated that any other model which can be represented or converted to an If-Then rule-based model may be employed. In embodiments, an If-Then rule-based model (or any other model which can be represented or converted to an If-Then rule-based model) utilizing the data derived from signals received by the electronic device 180 is used to determine one or more pre-existing characteristics, pre-existing state or both of the electrical circuit 200 and/or the absorbent article 230.

The extracts may include average percentage of increase between two or more consecutive increases in the magnitude or level of the data in the vertical axis over a length of time after connection between the electrical circuit 200 and the electronic device 180, allowable waiting time to search for a specific pattern in the data, consecutive number (or percentage) of extracts in a given length of time which are within a magnitude range in the vertical axis, which may be predetermined or determined during a training process.

Usage State

As an example, a rule in an If-Then rule-based model for determining whether a device 200 and an associated absorbent article 230 has previously been used or not may be of the following form: If $\alpha_1 < \alpha_1 < \alpha_2$ and $\alpha_3 < \alpha_2 < \alpha_4$ and $\alpha_5 < \alpha_3 < \alpha_6$ and $\alpha_7 < \alpha_4 < \alpha_8$ and ... and $\alpha_n < \alpha_m < \alpha_{n+1}$. Then the electrical circuit 200 and/or the absorbent article 230 is previously unused, where $\alpha_1, \alpha_2, \alpha_3 \ldots$, and $\alpha_m$ are the extracts and $\alpha_1, \alpha_2, \alpha_3, \ldots$, and $\alpha_{n+1}$ are the threshold values or percentages, which are predefined or are functions of one or more of the extracts.

For example, to identify whether an electrical circuit 200 or an absorbent article 230 is previously unused or reused, the magnitude of the data in the vertical axis, which are ordered according to the time at which they occur (e.g. time stamp), their sequential order or the like, should have a rising trend or should increase over a certain time and compared to predetermined thresholds. For example, for identifying a previously unused electrical circuit 200 and absorbent article 230, after connection between the electronic device 180 and the electrical circuit 200, the magnitude of the electrical variable or data derived therefrom in the vertical axis should start from a value below say 200 and five consecutive data points thereafter should also indicate a rising trend, thus indicating a previously unused electrical circuit 200 and absorbent article 230. For identifying a reused or previously used electrical circuit 200 and associated absorbent article 230, after connection between the electronic device 180 and the electrical circuit 200 the magnitude of the electrical variable or the data obtained therefrom in the vertical axis should start from a value above say 270 and five consecutive data points thereafter should also indicate an increasing trend, thus indicating a previously used electrical circuit 200 and absorbent article 230.

As illustrated in FIG. 6, the instability of the signal received by the electronic device 180 after connection with the electrical circuit 200 could be erroneously interpreted by the processor 102 to be multiple previously unused article or used article and disconnections rather than just signal instability. Signal instability may occur due to a loose connection. Embodiments of the invention are adapted to distinguish multiple physical connections and disconnections from signal instability by: filtering the detected disconnections/reconnections that are within a close time interval; the application of the method 100 for determining a characteristic of the article is delayed for a period of time after detecting a disconnection/reconnection; the If-Then rules for detection of a characteristic such as whether the electrical circuit 200 and the associated absorbent article 230 have previously been connected or not to the electronic device 180 are carried out. In the case of a state machine embodiment, discussed in more detail below, the new connection is detection of a specific number of disconnections followed by a number of specific extracts (with the first one starting from a value below a threshold) and the subsequent ones indicating an increasing trend.

If, during a training process, the magnitude of the data for a known previously unused and known reused combinations electrical circuits 200 and absorbent articles 230 start from a value below 200 and above 270, respectively, and both reach 710 for a small absorbent article size then the curve fitting which would be obtained during the training process (when the function is derived) would be of the following forms respectively: $f_{new}(x) = A_{new} - 1.5^{-(x-B_{new})}$, and $f_{used}(x) = A_{used} - 1.5^{-(x-B_{used})}$, where $A_{new} = 710$ with acceptable boundary of ±5, $B_{new} = 20$ with acceptable boundary of ±5, $A_{new} = 710$ with acceptable boundary of ±1, and $B_{new} = 15$ with acceptable boundary of +1.

For data obtained during an assessment phase from the connection of an electronic device 180 with an electrical circuit 200 and associated absorbent article 230 of unknown pre-existing characteristics, pre-existing state or both (i.e. unknown size and unknown usage state), to identify the size and previous usage state, a regression analysis of form $f(x) = a - 1.5^{-(x-d)}$ is performed to derive the extracts, a and d. The derived extracts are then checked in the following If-Then rule-based model to identify the electrical circuit 200 and associated absorbent article 230 usage state and size. The If-Then rule-based model is derived from the $f_{new}(x)$ and $f_{used}(x)$ from a training process. If $705 < a < 715$ and $19 < d < 21$, Then it is a previously unused electrical circuit 200 and absorbent article 230 with a small absorbent article 230 size. If $705 < a < 715$ and $14 < d < 16$, Then it is a previously used electrical circuit 200 and absorbent article 230 with a small absorbent article 230 size. In the above example x represents the sequence number of the data starting from 1 for a given point at which the regression analysis is going to be performed.

In the above example, for the function of form $$(x) = a - b^{-\frac{cx-d}{g}},$$

a and d are chosen as the electrical circuit 200 and absorbent article 230 extracts to be derived. However, it is to be appreciated that any one or more of the extracts a, b, c, d and g may be selected. It is to be appreciated that one or more of the extracts may have greater significance or relevance to the determination of the pre-existing characteristics, pre-existing state or both of the electrical circuit 200 and/or the absorbent article 230. The significance or relevance of the one or more extracts to the one or more pre-existing characteristics, pre-existing state or both of interest may be determined during a training process.

Absorbent Article Capacity

To identify the capacity of the absorbent article 230, after connection between the electronic device 180 and the electrical circuit 200 and associated absorbent article 230 the magnitude of the electrical variable or the data derived therefrom, or an average thereof over a given number of successive data points, in the vertical axis should fit within a specific range. For example, as illustrated in FIG. 6, the magnitude in the vertical axis of at least five successive data values determined after connection of the electrical circuit 200 and the associated absorbent article 230 to the electronic device 180 should be within a range of 700 to 745 for light capacity absorbent article 230, 750 to 795 for a moderate/medium capacity absorbent article 230 and 800 to 845 for large/heavy capacity absorbent article 230. Other pre-existing characteristics, pre-existing state or both of the electrical circuit 200 and the absorbent article 230 in which it is may be determined in a similar fashion depending on which range of values the magnitude of the data in the vertical axis stabilises or reaches equilibrium. Such pre-existing characteristics, pre-existing state or both may include electrical circuit 200 and/or absorbent article 230 size, manufacturer or other pre-existing characteristics or pre-existing state that may be determined from the electrical behaviour of the electrical circuit 200 and from training data obtained during a training process from electronic components 200 and absorbent articles 230 of known characteristics.

State Machines

According to embodiments of the invention, after the signal received by the electronic device 180 from the electrical circuit 200 is processed to generate data, a state machine function may be applied to the extracts (e.g. the extract here is the stream of the signal data). The state machine function comprises transitions between states. The state machine function includes transitional conditions that are predetermined or are determined during a training process. The transitional conditions may also be optimized in a post training process optimization process.

FIG. 5 illustrates an example of an electrical circuit 200 usage state detection process modelled by a state machine 300. The data is obtained from the electrical variable measured by the electronic device 180 after connection with the electrical circuit 200, which may include the magnitude of the data at selected points in time and/or a rising or falling trend of the data or a steady state at which the magnitude neither rises nor falls can be indicative of one or more pre-existing characteristics, pre-existing state or both, such as whether the absorbent article 230 and or the electrical circuit 200 has previously been connected to the electronic device 180 and, therefore, whether the absorbent article 230 and or the electrical circuit 200 has previously been used. The magnitude of the data of successive data points causes a transition in a state machine. The state machine 300 may be converted to an If-Then rule-based model. The possible path/s from the start point to an end state in the state machine can be translated into rules in an If-Then rule-based model.

After data is generated from electrical variables measured by the electronic device 180 after connection with the electrical circuit 200, which data may be represented as data point magnitude at period time intervals (i.e. time stamped). A first condition 310 is met where the magnitude at a data point is indicative of a disconnection between the electrical circuit 200 and the electronic device 180, which may indicate an unstable connection. A second condition 320 is met where the magnitude at a data point is below a maximum disconnection value indicative of no disconnection between the electrical circuit 200 and the electronic device 180. A third condition 330 is met where a data point is indicative of a signal being received by the electronic device 180, such as where the data point has a magnitude below a threshold such as below a magnitude of 200. When the third condition 330 is met this is indicative of a connection between the electronic device 180 and the electrical circuit 200. A fourth condition 340 is met where the magnitude of successive data points increases by a predetermined amount, such as 5%. A fifth condition 350 is met where the magnitude of successive data points increases by less than a predetermined amount, such as 5%, and is below a maximum disconnection value. Converted to the If-Then rule based model, If three successive data points meet the fourth condition, Then the usage state of the electrical circuit 200 is previously unused.

Figure 7:
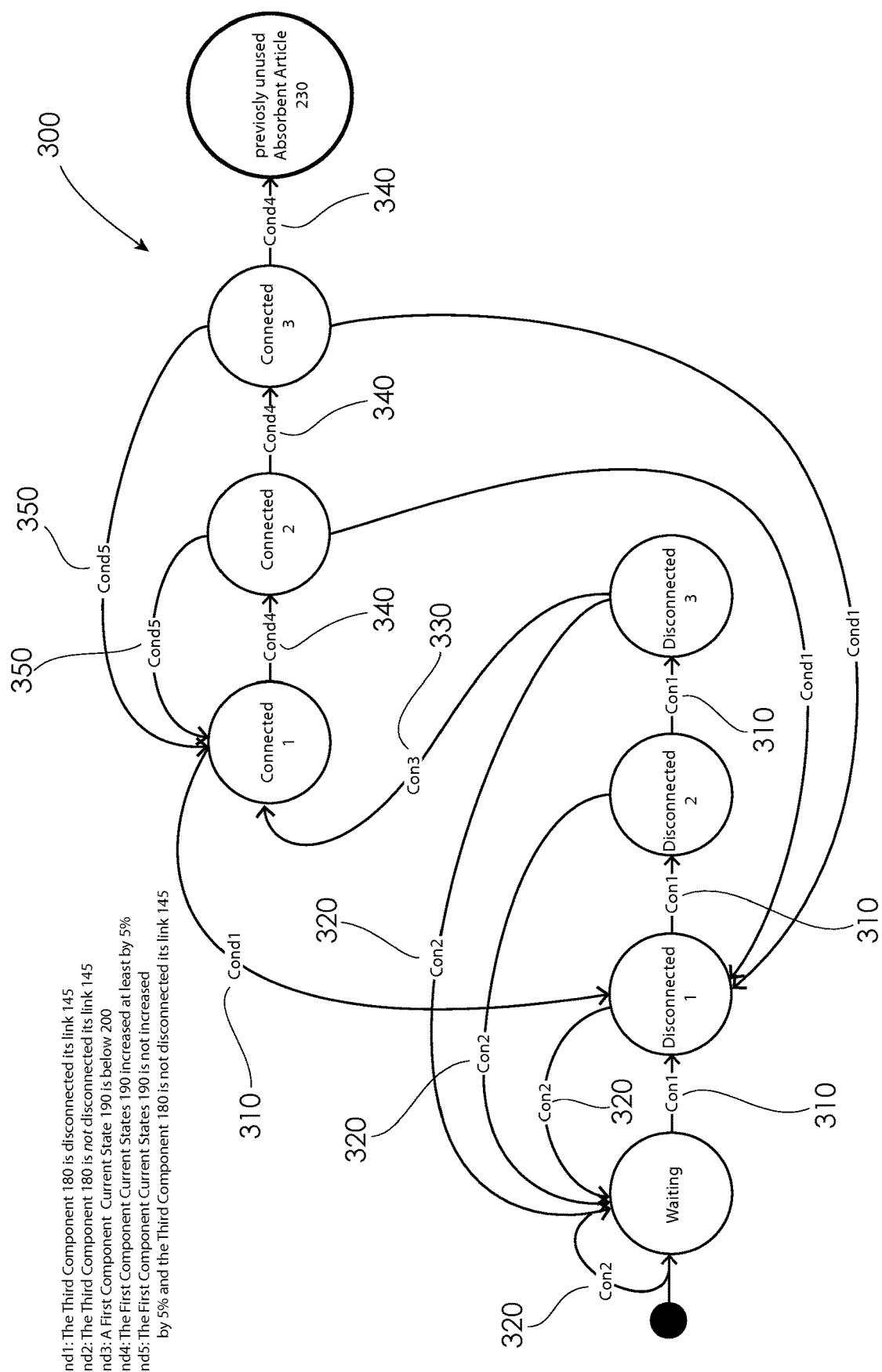
FIG. 7 illustrates an example of a state machine for determining a pre-existing state of a combination absorbent article and electrical circuit after connection to an electronic device wherein the If-Then rule based function includes comparing the data to the one or more thresholds which determine one or more state transitions in a state machine.

Expressed another way, the state machine illustrated in FIG. 7 can be converted to the following If-Then rule-based model;

IF ($data_t \geq data_{t-1}*1.05$) and ($data_{t-1} \geq data_{t-2}*1.05$) and ($data_{t-2} < 200$), and (max disconnection value $< data_{t-3} <$ max disconnection value), and (max disconnection value $< data_{t-4} <$ max disconnection value), Then electrical circuit 200 (and associated absorbent article 230) are previously unused, where $data_t$ is the set of the data point magnitude states and the data point magnitudes (i.e. disconnection states) in order of their occurrence (i.e. time stamp).

In further embodiments which are implemented by an If-Then rule-based model (or any other model that can be represented or translated into an If-Then rule-based model), the If-Then rule-based model may contain one or more rules. In another embodiment, none, one, or more of the operators (i.e. and, or, xor, not, etc.) may be used in each of the rules constituting the If-Then rule-based model. In another embodiment, none, one, or more conditions in one or more rules may apply operators of arity n in, where n is an integer. In yet another embodiment, none, one or more of the conditions may include linguistic expressions. In yet another embodiment, none, one, or more of the rules might be of fuzzy If-Then rule type. In yet another embodiment, one or more of the extracts is compared only to a lower or upper bound or both upper and lower bound thresholds.

In further embodiments, one or more If-Then rule-based models are aggregated. In yet another embodiment, the decision made from one or more of the If-Then rule-based models are aggregated and form one or more value or percentage and then the value/s and/or the percentages are compared to a lower or upper bound or both upper and lower bound thresholds.

In an embodiment, one or more of the absorbent article capacity detection example, absorbent article and/or sensor device size detection, absorbent article and/or sensor device usage state and absorbent article manufacturer detection examples are modelled by a curve-fitting analysis (i.e. regression analysis, neural networks, decision trees, and so on) or other classification algorithms, or statistical approaches, state machines or the likes that can be converted or translated into If-Then rule based model.

It is to be understood that part or all of the functionality of the processor 102 may be carried out via a processor contained within the portable/wearable electronic device 180 or may be distributed over central and/or remote devices connected via a wired or wireless connection in a cloud computing environment.

Optimization

As mentioned above, data input to the system 100 is used in some embodiments to provide training data for carrying out an optimization process. By such an optimization process, the function and the extracts derived during the training phase can be refined or improved (i.e. optimized) during an optimization procedure that utilizes a set of training data obtained during a training process or using training data obtained during the assessment phase.

In some embodiments the state machine function comprises transitions between states. The state machine function includes transitional conditions that are predetermined or are determined during a training process. The transitional conditions can also be refined or improved (i.e. optimized) in a post training process optimization process.

Aspects of the optimization process may include investigating discrepancies between the characteristics of the electronic device determined by the method and system with observed, known characteristics and modifying the initial state machine flow, to cater for dealing with the discrepancies. This process can be carried out iteratively until a desired performance is obtained.

Also, instead of applying a state machine function with a predefined flow, an optimization procedure may be employed to optimize both the flow and the transition conditions. The optimization procedure is intended to determine the optimized number of states and the optimized transition conditions from each state to another state or to itself. The optimization procedure involves comparing extracts derived during the training phase with extracts derived from known characteristics of the electronic device such that the performance of the state machine function can be optimized.

If there more than one performance values need to be optimized then: 1) the performance values can be combined to form a single value, either linearly or non-linearly, wherein the relative importance of a value over other values may be expressed by considering greater weights for that function; and 2) the performance values treated separately by a multi-objective optimization procedure, (example of two performance value is; sensitivity and specificity in which the sensitivity and specify can form a single value such as f-measure).

Further Embodiments

Other embodiments of the present invention can involve determining a pre-existing characteristic or pre-existing state of an electrical circuit and absorbent article combination wherein the absorbent article includes a diaper, a menstrual pad, a wound care pad and any other device or article adapted to absorb fluid. Other embodiments of the absorbent article include any article that is adapted to be used with another device and disposed of or otherwise treated after use (i.e. is not intended to be reused) such as coffee pods for use with a coffee brewing machine or the like.

The invention claimed is:

1. A method for determining if a combination absorbent article and electrical circuit of an incontinence monitoring system has been previously connected to a signal source of an electronic device and providing an alert, wherein the absorbent article is adapted for absorbing the product of an incontinence event and the electrical circuit is adapted for exhibiting an electrical response in the presence of the product of an incontinence event, the method including:
measuring an electrical variable after electrical connection of the signal source of an electronic device to the combination article and electrical circuit to generate data indicative of the electrical variable at sequential time values; and
processing the data with a processor including applying a curve fitting function to the data to generate extracts and applying an If-Then rule based function comprising two or more thresholds to determine if the combination absorbent article and electrical circuit has been previously connected to the signal source of the electronic device according to whether:
an extract is above or below one threshold after connection of the electronic device to the combination article and electrical circuit, and
an extract subsequently exhibits an increasing trend gradient that is greater and/or less than another threshold; and
providing an alert if the combination absorbent article and electrical circuit has been previously connected to the electronic device.

2. The method of claim 1, wherein each of the thresholds determines one or more state transitions in a state machine function.

3. The method of claim 1, wherein time intervals between consecutive time values are shorter during an early phase after connection of the electronic device to the combination article and electrical circuit than during a later phase.

4. The method of claim 1, wherein the electrical variable includes capacitance of a capacitor and resistance of a resistor in the electrical circuit.

5. The method of claim 1, wherein the electrical variable includes any one or more of electrical charge stored on a capacitor, voltage or current.

6. The method of claim 1, wherein the method includes determining one or more other pre-existing characteristics, pre-existing states or both including any one or more of:
capacity of the absorbent article and the electrical circuit; and
type of the absorbent article and the electrical circuit or type of the electrical circuit.

7. The method of claim 6, wherein the type of the absorbent article and the electrical circuit or the type of the electrical circuit includes absorbent article construction information.

8. The method of claim 1, wherein if the data is between two thresholds after connection of the electronic device to the combination article and electrical circuit then the If-Then rule based function determines the capacity of the absorbent article and the electrical circuit.

9. The method of claim 1, further including transmitting the pre-existing characteristic, the pre-existing state or both of the combination article and electrical circuit to an electronic device for presentation to a user.

10. The method of claim 1, further including utilising the pre-existing characteristic, the pre-existing state or both of the combination article and electrical circuit in a method and or system for determining any one or more of:
the occurrence of wetness events in the absorbent article;
wetness event volume for a wetness event occurring in the absorbent article; and
that a combination absorbent article and electrical circuit being worn by a subject requires changing.

11. The method of claim 1, wherein processing the data includes generating a plurality of pre-existing states at respective times and determining the pre-existing state includes selecting a subset from the plurality of pre-existing states.

12. The method of claim 1, including sampling the electrical variable at shorter time intervals during an initial phase after electrical connection of the signal source of the electronic device to the combination article and electrical circuit and at longer time intervals during a subsequent phase.

13. An incontinence monitoring system adapted for providing an alert if a combination absorbent article and electrical circuit has been previously connected to an electronic device, the system including:

a combination absorbent article and electrical circuit, wherein the absorbent article is adapted for absorbing the product of an incontinence event and the electrical circuit is adapted for exhibiting an electrical response in the presence of the product of an incontinence event;

an electronic device electrically connectable to the combination absorbent article and electrical circuit for measuring an electrical variable after connection of the electronic device to the combination article and electronic component to generate data indicative of the electrical variable at sequential time values, a processor for processing the data including applying a curve fitting function to the data to generate extracts and applying an If-Then rule based function comprising two or more thresholds to determine if the combination absorbent article and electrical circuit has been previously connected to the electronic device according to whether an extract is above or below one threshold after connection of the electronic device to the combination article and electrical circuit, and an extract subsequently exhibits an increasing trend gradient that is greater and/or less than another threshold; and providing an alert if the combination absorbent article and electrical circuit has been previously connected to the electronic device.

14. The system of claim 13, wherein the processor is configured to process the data to determine any one or more of:

the occurrence of wetness events in the absorbent article;

wetness event volume for a wetness event occurring in the absorbent article; and that a combination absorbent article and electrical circuit being worn by a subject requires changing.

15. The system of claim 13, including a display for displaying the pre-existing characteristic, the pre-existing state or both of the combination article and electrical circuit for presentation to a user.

16. The system of claim 13, including a mobile electronic device including a display for receiving and displaying the pre-existing characteristic, the pre-existing state or both of the combination article and electrical circuit for presentation to a user.

17. The system of claim 13, wherein the electronic device includes electrical contacts for electrically connecting with electrical contacts of the combination absorbent article and electrical circuit.

18. The system of claim 13, wherein the electronic device is configured to sample the electrical variable at shorter time intervals during an initial phase after electrical connection of the signal source of the electronic device to the combination article and electrical circuit and at longer time intervals during a subsequent phase.

19. The system of claim 18, wherein the sampling intervals are determined in a training phase.

* * * * *